United States Patent
Weller

(10) Patent No.: US 9,687,305 B2
(45) Date of Patent: Jun. 27, 2017

(54) LIGHTING DEVICE

(75) Inventor: Matthias Weller, Rosdorf (DE)

(73) Assignee: ONDAL HOLDING GMBH, Hunfeld (DE)

( * ) Notice: Subject to any disclaimer, the term of this patent is extended or adjusted under 35 U.S.C. 154(b) by 138 days.

(21) Appl. No.: 13/823,689

(22) PCT Filed: Jan. 13, 2012

(86) PCT No.: PCT/EP2012/000145
§ 371 (c)(1),
(2), (4) Date: Apr. 11, 2013

(87) PCT Pub. No.: WO2012/095323
PCT Pub. Date: Jul. 19, 2012

(65) Prior Publication Data
US 2013/0281792 A1    Oct. 24, 2013

(30) Foreign Application Priority Data

Jan. 14, 2011 (EP) .................................... 11000286

(51) Int. Cl.
| | | |
|---|---|---|
| *F21S 4/00* | (2016.01) | |
| *A61B 19/00* | (2006.01) | |
| *F21V 23/04* | (2006.01) | |
| *A61B 90/30* | (2016.01) | |

(Continued)

(52) U.S. Cl.
CPC .......... *A61B 19/5202* (2013.01); *A61B 90/30* (2016.02); *F21V 23/04* (2013.01); *F21W 2131/20* (2013.01); *F21W 2131/205* (2013.01)

(58) Field of Classification Search
CPC ................ A61B 19/5202; F21V 23/04; F21W 2131/20; F21W 2131/205
USPC ....... 362/269, 285, 287, 370, 371, 404, 427, 362/804, 249
See application file for complete search history.

(56) References Cited

U.S. PATENT DOCUMENTS 3,378,678 A * 4/1968 De Groff ................ F21V 21/00
                                                  362/12
3,599,922 A * 8/1971 Junginger ..................... 248/313
(Continued)

FOREIGN PATENT DOCUMENTS

CN       1643298 A       7/2005
CN       1662771 A       8/2005
(Continued)

*Primary Examiner* — Jong-Suk (James) Lee
*Assistant Examiner* — Tsion Tumebo
(74) *Attorney, Agent, or Firm* — Seed IP Law Group LLP

(57) ABSTRACT

A lighting device for a medical treatment room having a support frame configured to be mounted to a wall or ceiling of the medical treatment room. A first illumination unit on the support frame is configured to provide direct illumination of an operating area and a second illumination unit on the support frame is configured to provide indirect illumination of the operating area. The support frame can be articulated for movement of the first and second illumination units. Movement of the support frame is adapted to activate and deactivate the first and second illumination units. Thus, the lighting device includes a control unit configured to switch the first and second illumination units on and/or off when the support frame is moved relative to the operating area.

7 Claims, 1 Drawing Sheet

(51) Int. Cl.
*F21W 131/20* (2006.01)
*F21W 131/205* (2006.01)

(56) References Cited

U.S. PATENT DOCUMENTS

| | | | | |
|---|---|---|---|---|
| 4,437,144 A | * | 3/1984 | Guenther | F16M 11/10 362/269 |
| 4,517,632 A | * | 5/1985 | Roos | 362/389 |
| 4,581,689 A | * | 4/1986 | Oram | 362/275 |
| 4,816,969 A | * | 3/1989 | Miller | F21S 8/033 362/130 |
| 4,884,008 A | * | 11/1989 | Bossler et al. | 315/152 |
| 5,038,261 A | * | 8/1991 | Kloos | F21V 21/14 362/286 |
| 5,539,626 A | * | 7/1996 | Scholz | F21V 23/04 362/237 |
| 6,012,821 A | * | 1/2000 | Yeaney | F16M 11/04 248/325 |
| 6,160,582 A | * | 12/2000 | Hill | H05B 37/02 348/370 |
| 6,402,235 B1 | * | 6/2002 | Letendre | 297/195.1 |
| 6,464,383 B1 | * | 10/2002 | Northington | A61B 19/52 362/552 |
| 7,224,472 B2 | * | 5/2007 | Bauch et al. | 356/611 |
| 7,390,105 B2 | * | 6/2008 | Nelson | F21V 21/088 362/198 |
| 8,147,092 B2 | * | 4/2012 | Wu et al. | 362/231 |
| 8,292,804 B2 | * | 10/2012 | Marka | F21V 23/0464 600/249 |
| 2002/0015296 A1 | * | 2/2002 | Howell et al. | 362/11 |
| 2003/0161152 A1 | | 8/2003 | Jesurun et al. | |
| 2003/0165053 A1 | * | 9/2003 | Wasow | F21V 19/04 362/20 |
| 2003/0210559 A1 | * | 11/2003 | Jesurun et al. | 362/572 |

FOREIGN PATENT DOCUMENTS

| | | |
|---|---|---|
| DE | 93 17 671 U1 | 2/1994 |
| EP | 1 536 179 A2 | 6/2005 |
| WO | 99/26017 A1 | 5/1999 |

* cited by examiner

LIGHTING DEVICE

TECHNICAL FIELD

The present invention relates to a lighting device for a medical treatment room, such as a medical surgery or an operating theatre.

More particularly, the invention relates to a lighting device that is designed to be mounted or suspended from a ceiling or from a wall of the medical treatment room for illuminating an operating area of the medical personnel.

BACKGROUND OF THE INVENTION

Traditionally, lighting units for operating theatres include one or more lamps that are designed to shine light onto the operating area to brightly illuminate that part of a patient currently being treated by the medical personnel. Where surgery is involved, for example, the lamps enable doctors and nurses operating on the patient to have a clear and well illuminated view of the surgical procedure. In this connection, it has been typical to promote increased or enhanced illumination of the operating area. Indeed, by having multiple lamps shining on the operating area at different angles, it has been possible to substantially overcome issues of shadows and shading.

Importantly, however, the nature of medical interventions has changed significantly over the years. The tools used by medical personnel in performing their procedures today are not always favoured by a bright illumination of the operating area. Where endoscopic cameras are used, for example, the medical staff are reliant upon images displayed on monitors for assessing the condition of the patient and/or the progress of the procedure. As the monitors themselves display light-generated images, a highly illuminated ambient environment can compromise the viewing of the images displayed and can create reflections on the glass screen of the monitor that interfere with the medical personnel's view of the images. Thus, there is a need to develop a new and improved lighting device for medical treatment rooms, such as medical surgeries and operating theatres, which is adapted to the needs of modern treatment equipment. The present invention is directed to providing such a lighting device.

SUMMARY OF THE INVENTION

According to one broad aspect, the present invention provides a lighting device for a medical treatment room, such as a surgery or an operating theatre, comprising: a support frame configured to be fixed to a wall or a ceiling of a medical treatment room; at least one first illumination unit mounted on the support frame for directly illuminating an operating area in the room; and at least one second illumination unit mounted on the support frame for indirectly illuminating the operating area; wherein the support frame is adapted for movement relative to the operating area to position the first and second illumination units, and wherein movement of the support frame is adapted to activate and/or to deactivate the first and second illumination units.

In a particularly preferred form of the invention, the support frame of the lighting device has a first position, in which the first illumination unit is "on" or activated and the second illumination unit is "off" or deactivated, and a second position in which the second illumination unit is "on" or activated and the first illumination unit is "off" or deactivated. In this embodiment, movement of the support frame from the first position to the second position operates to switch off the first illumination unit and to switch on the second illumination unit. On the other hand, movement of the support frame from the second position to the first position operates to switch off the second illumination unit and to switch on the first illumination unit. In a preferred form of the invention, the first position of the lighting device is higher or more elevated than the second position.

In a preferred form of the invention, the lighting device is in the first position when the support frame (e.g. arm member) extends at an angle $\alpha$ with respect to a vertical axis, and the lighting device is in the second position when the support frame (e.g. arm member) extends at an angle $\beta$ with respect to the vertical axis. The angle $\alpha$ is larger than the angle $\beta$. For example, the angle $\alpha$ may be greater than 90° (e.g. 100°<$\alpha$<160°) whereas the angle $\beta$ may be smaller than 90° (e.g. 50°>$\beta$>90°). The angles $\alpha$ and $\beta$ desirably extend between (i.e. are subtended by) a vertical axis and an upper side of an arm member of the support frame.

In a preferred form of the invention, the lighting device is adapted to be manipulated manually to move the support frame relative to the operating area. In this regard, it will be appreciated that while one part of the support frame is to be fixed to a wall or ceiling of the medical treatment room, another part of the support frame is movable relative to the fixed part, e.g. via joints, to move the illumination units relative to the operating area. To this end, the lighting device preferably comprises a handle for manual movement of the support frame and the first and second illumination units relative to the operating area. That is, a surgeon or other medical professional may manipulate the lighting device by hand during the course of an operating procedure to alter the lighting conditions depending on the progress of the procedure and the nature of the particular tools currently in use.

According to another broad aspect, the present invention provides a lighting device for a medical treatment room, such as a medical surgery or an operating theatre, comprising: a support frame which is configured to be secured to a wall or to a ceiling of the treatment room; a first illumination unit provided on the support frame configured to provide direct illumination of an operating area in the treatment room; and a second illumination unit provided on the support frame and configured to provide indirect illumination of the operating area. The support frame is articulated for movement of the first and second illumination units relative to the operating area, and the lighting device comprises a controller or a control unit which is configured to switch the first and second illumination units on and/or off when the support frame is moved to a predetermined extent or degree relative to the operating area.

In a preferred form of the invention, the support frame is configured to be mounted above the operating area and the first illumination unit is arranged on the support frame to shine light downwardly onto the operating area. The support frame typically includes an arm member, and the first illumination unit may be mounted at an end region of the arm member. The arm member may be articulated such that it is configured for pivotal movement about a substantially horizontal axis and/or about a substantially vertical axis. In that case, the controller may be configured to switch the first and second illumination units on and/or off upon pivotal movement of the support frame through a predetermined angle about said axis. In another preferred form of the invention, the arm member of the support frame may be configured for movement in a translational (e.g. axial) extension and retraction, with the controller or control unit being configured to be activate or to deactivate the first and/or second illumination unit upon a translational extension or retraction of the arm member to a predetermined extent.

In a preferred form of the invention, the controller or control unit is configured to switch on the first illumination unit when the support frame is moved towards the operating area to a predetermined extent, e.g. through a predetermined angle about a pivot axis. Similarly, the controller or control unit may be configured to switch off the first illumination unit when the support frame is moved away from the operating area to a predetermined extent or degree, e.g. through a predetermined angle about a pivot axis.

Preferably, a trigger signal for the controller to switch off the first illumination unit also operates to switch on the second illumination unit. Similarly, a trigger signal for the controller to switch on the first illumination unit preferably also operates to switch off the second illumination unit. Thus, the controller is desirably adapted to switch between the first and second illumination units, such that when one of the first and second illumination units is switched on or activated, the other is switched off or deactivated. For example, therefore, when the support frame is moved away from the operating area to a predetermined extent to switch off the first illumination unit, the second illumination unit is switched on. When the support frame is moved towards the operating area to a predetermined extent to switch on or activate the first illumination unit, the second illumination unit is switched off or deactivated.

In a preferred form of the invention, the first illumination unit comprises one or more lamps and a reflector arrangement configured to shine light generated by the lamps directly onto the operating area. The second illumination unit, on the other hand, is arranged on the support frame to shine light upwardly away from the operating area. In this connection, the second illumination unit is desirably provided on a side of the support frame facing away from the operating area. For example, the second illumination unit may be provided on an upper side of the articulated arm member and may include a reflector that directs or shines light from the second illumination unit upwards and away from the operating area.

It should be noted that the terms "upper", "lower", "above", "below", "upwards", and "downwards" and other similar terms used herein in respect of various parts of the lighting device of the invention are intended to be given their ordinary meaning in view of the normal or in-use orientation of the device described herein. It will be appreciated, however, that other interpretations of these terms may be appropriate depending on the orientation of the device or its respective parts at the time.

BRIEF DESCRIPTION OF THE DRAWINGS

The above and further features and advantages of the invention will become more readily apparent from the following detailed description of preferred embodiments of the invention with reference to the accompanying drawings, in which like reference characters identify like features, and in which.

DETAILED DESCRIPTION OF THE PREFERRED EMBODIMENTS

Figure 1:
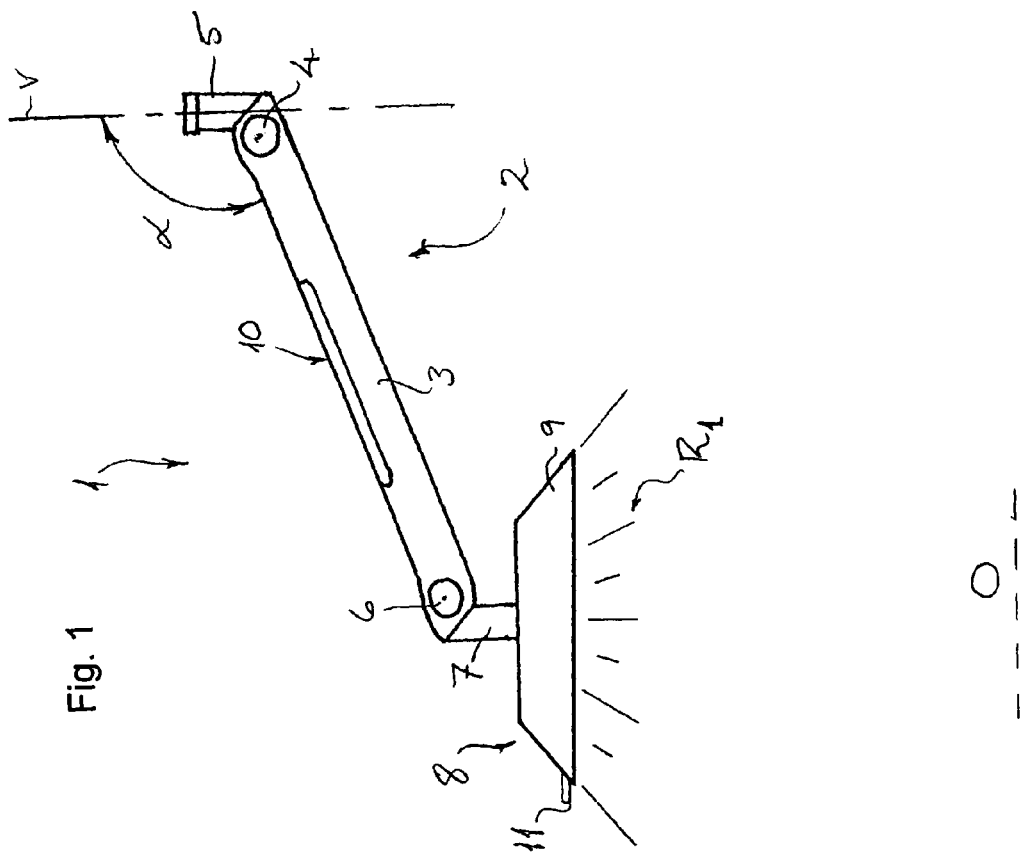
FIG. 1 is a schematic side view of a lighting device according to an embodiment of the present invention shown in a first position.

With reference to FIG. 1 of the drawings, a lighting device 1 according to a preferred embodiment of the invention is shown in a first position. The lighting device 1 comprises a support frame 2 which, in this embodiment, includes an elongate arm member 3 that is connected at one end via a pivot or hinge joint 4 with a vertically extending stud shaft 5 for connection to a fixture (not shown) rigidly secured to a wall or a ceiling of the medical surgery or operating theatre. The stud shaft 5 may desirably incorporate a pivot bearing configured for rotational movement about the substantially vertical axis V. The arm member 3 of the support frame 2 is furthermore connected at its opposite end via a pivot or hinge joint 6 with a substantially vertically depending connection element 7 described below. The arm member 3 is thus articulated via the pivot joints 4, 6 and the rotatable stud shaft 5 for movement relative to the fixture at which the lighting device 1 is secured to the wall or ceiling of the room.

A first illumination unit 8 is attached to the support frame 2 via the connecting element 7. In this way, the first illumination unit 8 is suspended from the support frame 2 at the free end of the arm member 3. The first illumination unit 8 comprises a plurality of lamps (not shown) and a reflector arrangement within a housing 9 and is configured to shine light downwardly onto an operating area O below the lighting device 1. The rays of light $R_1$ shining from the first illumination unit 8 are illustrated schematically in FIG. 1. In this regard, in FIG. 1 of the drawings the lighting device 1 is shown in a first position, in which the mounting arm 3 subtends an angle $\alpha$ with the vertical axis V extending upwardly from the end of the arm 3 at the stub shaft 5. In this first position, the first illumination unit 8 is activated or switched on such that it directly illuminates the operating area O below the lighting device 1.

Also provided on the support frame 2 is a second illumination unit 10 which, in this embodiment, has an elongate configuration and is mounted on an upper side of the arm member 3. The second illumination unit 10 comprises one or more lamp, e.g. in the form of an elongate fluorescent tube or light emitting diodes (LEDs), combined with an upwardly directed reflector. In this way, the second illumination unit 10 is oriented and configured to shine light in an upward direction, i.e. away from the operating area O located below the lighting device 1. Thus, the second illumination unit 10 is configured to provide only indirect illumination of the operating area O and the rays of light $R_2$ shining from the second illumination unit 10 are illustrated schematically in FIG. 2.

Figure 2:
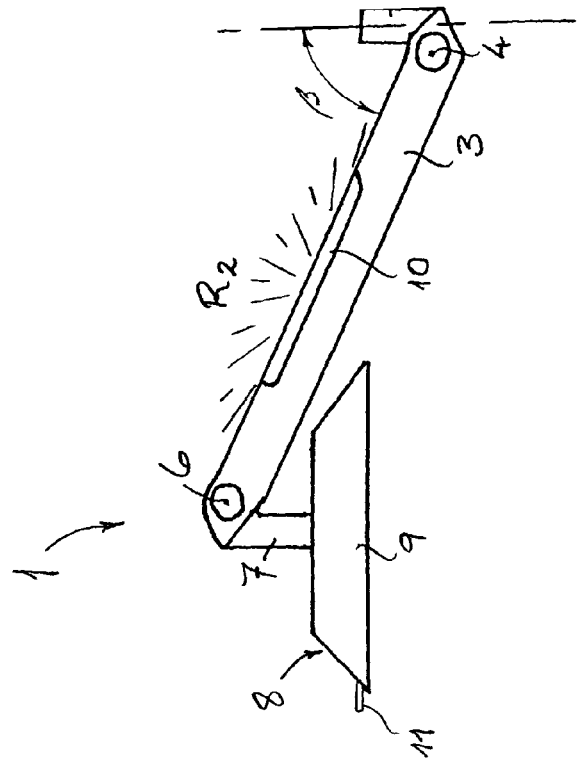
FIG. 2 is a side view of the lighting device of FIG. 1 shown in a second position.

With reference now to FIG. 2 of the drawings, the lighting device 1 is shown in a second position. That is, the arm member 3 has been pivoted upwards at the joint 4 from the first position shown in FIG. 1 such that the arm member 3 now subtends a smaller angle $\beta$ with the vertical axis V extending upwardly from the end of the arm 3 at the stub shaft 5. In this second position, therefore, the first illumination unit 8 has been elevated and thus moved somewhat away from the operating area O. This movement of the lighting device 1 from the first position to the second position can be achieved manually by the medical staff; for example, via a handle 11 which in this case is provided on the housing 9 of the first illumination unit 8. That is, a medical professional standing in the operating area O under the lighting device 1 can simply grip the handle 11 and lift the lighting device 1 from the first position to the second position. The arm member 3 is preferably balanced, e.g. via spring means or via a counterweight or via pressure and friction, so that it can be moved without substantial effort and so that it maintains the position to which it is moved. In this regard, the arm member 3 can include a plurality of elements which cooperate with e.g. spring means to provide the balanced arrangement. For example, the arm member 3 may comprise elongate elements in a parallelogram configuration.

According to this embodiment of the invention, when the lighting device 1 is moved from the first position in FIG. 1 to the second position in FIG. 2, the first illumination unit 8 at the free end of the arm member 3 is deactivated or switched off and the second illumination unit 10 mounted on the upper side of the arm member 3 is activated or switched on. Similarly, when the lighting device 1 is moved from the second position in FIG. 2 to the first position shown in FIG. 1 (i.e. again by manual manipulation via the handle 11), the first illumination unit 8 is switched on and the second illumination unit 10 is switched off. In other words, the lighting device 1 of the invention incorporates a control unit for activating and deactivating the two illumination units 8, 10 depending upon the positioning of the device 1 by the medical personnel. In this example, when a surgeon requires direct illumination of the operating area O, the handle 11 is used to pull the lighting device to the first position shown in FIG. 1. In this position the first illumination unit 8 is switched on and the operating area O is directly and brightly illuminated. If, on the other hand, the surgeon wishes to carry out an endoscopic procedure and requires dimmed lighting for better observation of the images displayed on a monitor, the lighting device can be easily lifted via the handle 11 to the second position, in which the first illumination unit 8 is switched off and the second illumination unit 10 is switched on to provide a dimmed, indirect lighting in the operating area.

It will be appreciated that the above description of the preferred embodiments of the invention with reference to the drawings has been made by way of example only. Thus, a person skilled in the art will appreciate that various changes, modifications and/or additions may be made to the parts particularly described and illustrated without departing from the scope of the invention as defined in the claims.

The invention claimed is:

1. A lighting device for use in a medical treatment room, comprising:
    a support frame configured to be fixed to a wall or to a ceiling of the medical treatment room;
    a control unit;
    at least one first illumination unit mounted on the support frame configured to provide direct illumination of an operating area in the treatment room; and
    at least one second illumination unit mounted on the support frame and configured to provide indirect illumination of the operating area;
    wherein the support frame is adapted for movement relative to the operating area to position the first and second illumination units, and
    wherein the control unit is configured to activate the first illumination unit while deactivating the second illumination unit or activate the second illumination unit while deactivating the first illumination unit in response to movement of the support frame relative to the operating area.

2. A lighting device according to claim 1, wherein the support frame of the lighting device has a first position in which the first illumination unit is "on" or activated and the second illumination unit is "off" or deactivated, and a second position in which the second illumination unit is "on" or activated and the first illumination unit is "off" or deactivated.

3. A lighting device according to claim 2, wherein movement of the support frame from the first position to the second position operates to deactivate or switch off the first illumination unit and to activate or switch on the second illumination unit.

4. A lighting device according to claim 2, wherein movement of the support frame from the second position to the first position operates to deactivate or switch off the second illumination unit and to activate or switch on the first illumination unit.

5. A lighting device according to claim 2, wherein the first position of the lighting device is higher or more elevated than the second position.

6. A lighting device according to claim 2, wherein the lighting device is in the first position when the support frame extends at an angle $\alpha$ with respect to a vertical axis, and wherein the lighting device is in the second position when the support frame extends at an angle $\beta$ with respect to the vertical axis, the angle $\alpha$ being larger than the angle $\beta$.

7. A lighting device for use in a medical treatment room, comprising:
    a support frame configured to be mounted to a wall or to a ceiling of the medical treatment room;
    a control unit;
    a first illumination unit provided on the support frame and configured to provide direct illumination of an operating area in the treatment room; and
    a second illumination unit provided on the support frame and configured to provide indirect illumination of the operating area;
    wherein the support frame is adapted for movement of the first and second illumination units relative to the operating area, and
    wherein the control unit is configured to:
        switch the first illumination unit to an on configuration while switching the second illumination unit to an off configuration when the support frame is rotatably moved at an angle $\alpha$ relative to a vertical axis of the lighting device; and
        switch the second illumination unit to an on configuration while switching the first illumination unit to an off configuration when the support frame is moved at an angle $\beta$ relative to the vertical axis, the angle $\alpha$ being greater than the angle $\beta$.

* * * * *

UNITED STATES PATENT AND TRADEMARK OFFICE
CERTIFICATE OF CORRECTION

PATENT NO. : 9,687,305 B2
APPLICATION NO. : 13/823689
DATED : June 27, 2017
INVENTOR(S) : Matthias Weller It is certified that error appears in the above-identified patent and that said Letters Patent is hereby corrected as shown below:

In the Claims

Column 6, Line 54:
"an angle βrelative to the vertical axis, the angle α"
Should read:
--an angle β relative to the vertical axis, the angle α--.

Signed and Sealed this
Twenty-third Day of January, 2018

Joseph Matal
*Performing the Functions and Duties of the*
*Under Secretary of Commerce for Intellectual Property and*
*Director of the United States Patent and Trademark Office*